United States Patent [19]

Howe et al.

[11] Patent Number: 4,771,446

[45] Date of Patent: Sep. 13, 1988

[54] GRADING ORIENTATION ERRORS IN CRYSTAL SPECIMENS

[76] Inventors: Stephen Howe, 13D Venice Court, 41 Conduit Road, Hong Kong; Donald Rogers, 11 Salvington Crescent, Bexhill-on-Sea, East Sussex, both of United Kingdom

[21] Appl. No.: 894,687

[22] Filed: Aug. 8, 1986

[30] Foreign Application Priority Data

Mar. 26, 1986 [GB] United Kingdom ............... 8607481

[51] Int. Cl.⁴ .......................................... G01N 23/207
[52] U.S. Cl. ........................................ 378/73; 378/77; 378/76
[58] Field of Search ................... 378/71, 73, 76, 81, 378/77

[56] References Cited

U.S. PATENT DOCUMENTS

| | | | |
|---|---|---|---|
| 3,649,831 | 3/1972 | Eckerlin | 378/76 |
| 3,870,880 | 3/1975 | Merigoux et al. | 378/81 |
| 4,301,364 | 11/1981 | Goebel | 378/73 |
| 4,412,345 | 10/1983 | Workman et al. | 378/81 |
| 4,637,041 | 1/1987 | Brinkgreve et al. | 378/81 |

*Primary Examiner*—Carolyn E. Fields
*Assistant Examiner*—David P. Porta
*Attorney, Agent, or Firm*—Kane, Dalsimer, Sullivan, Kurucz, Levy, Eisele and Richard

[57] ABSTRACT

The invention comprises a method of, and apparatus for, measuring the orientation error in a single crystal. An X-ray beam is reflected from the surface of the crystal while it is rotated, and the orientation error is determined from the figure traced at a detector by the reflected beam. The orientation error may be calculated from the major axes of the traced figure, or, if the X-ray beam contains a characteristic line, from the separation of the two bright spots produced in the traced figure.

13 Claims, 10 Drawing Sheets

GRADING ORIENTATION ERRORS IN CRYSTAL SPECIMENS

This invention relates to a method of and apparatus for identifying the orientation errors in single crystals, more particularly, though not exclusively, semi-conductor wafers. It further relates to the grading of the orientation errors in crystal specimens.

Our copending patent application Nos. PCT GB/84/003245 and U.K. 8508060 relate to the setting and/or determination of of the orientation of a crystal to a high degree of accuracy, so enabling precise setting of the crystal prior to cutting, polishing of whatever, to produce a high quality product having predetermined properties/characteristics.

The present invention proposes a different approach, immediately applicable to current production techniques. By identifying the orientation error of large numbers of crystals such as semi-conductor wafers prior to growing epitaxial layers thereon, it is possible to grade the crystals into batches for appropriate subsequent processing so yielding more uniform and predictable results.

Wafers, when bought in by integrated circuit manufacturers, are often inspected for thickness, relative flatness (checked optically); surface defects, dislocations, contamination (checked optically); and virgin resistivity (using eddy currents); but no attempt is made to estimate the magnitude of the cutting (or orientation) error i.e. the angle between the cut or polished face and the desired crystallographic planes or, what is the same thing, the angle between the corresponding reciprocal-lattice vector and the normal to the surface about to be coated. As the rate of deposition of epitaxial layers on that surface depends on this angle, it is desirable in the interests of uniformity of deposits (and therefore of switching properties), to grade the wafer errors and to give each batch an appropriate deposition time. The present invention allows the cutting error in a wafer to be graded in a matter of seconds and can be performed either on a one-off manual basis or made fully automatic for a production line. Either way the time spent on this new inspection is trivial compared to the currently used inspections and could well improve the quality control of the finished wafers. It can readily be extended to check the uniformity of orientation over a whole wafer, a matter of some importance for the very large wafers now being made or developed.

In addition to wafers, the invention is applicable to any other crystalline material e.e. quartz and other oscillator crystals, or laser and other opto-electronic materials, where it is desired to know how closely a prepared surface approximates to certain lattice planes. In principle, there is no restriction on crystal symmetry or on the type of planes.

In accordance with the present invention we propose a method for identifying or measuring the orientation error in a crystal, for example, a semi-conductor wafer, comprising the steps of directing a beam of X-rays, preferably a narrow collimated beam of unfiltered X-rays, onto a prepared surface of the crystal while relatively rotating the crystal and the beam about an axis normal to the surface usually at the point of impingement, and detecting the reflectedbeam on a plane- or line-detector set in symmetry with the incident beam and with the plane of the detector perpendicular to the reflected beam. The angle of incidence ($\theta$) of the X-ray beam is preferably in the region of 45°.

The invention also includes apparatus for identifying and/or measuring orientation errors in a crystal specimen, the apparatus comprising a source of a beam of X-rays, a crystal specimen support, means for relatively rotating the X-ray source being arranged to direct a beam of X-rays toward the specimen support at an angle ($\theta$) to the axis of relative rotation, and a plane- or line-detector arranged in symmetry with the X-ray source about the said axis to receive reflexions from a prepared surface of the crystal specimen normal to the axis of relative rotation.

Any angular error ($\delta$) between the prepared surface and the crystallographic planes causes the reflected ray to trace a loop on the detector screen as the specimen rotates. The dimensions of the loop are used to measure or grade the error: the preferred method depends on the application.

The length of the major axis of the loop depends only on $\delta$, the error, and is independent of $\theta$, but, as it involves two wavelengths, the X-ray system must deliver and detect both wavelengths, i.e. white radiation is preferred. A mask may be used to grade specimens according to the length of the major axis or it may be measured manually with a graticule or (automatically) with a linear position-sensitive detector.

If measurement is made on the minor axis of the loop, the wavelength now covers only a narrow range but as the length of the minor axis depends on both $\theta$ and $\delta$, this axis is less easy to use.

It is specially convenient if $\theta$ is preset for reflection of characteristic radiation from a perfectly set specimen. Then all that is needed is to measure the separation of the two bright spots on the loop which are close to but not necessarily on the minor axis. It is possible to use a graticule or 1-D position sensitive detector.

Grading and measurements as described above are easily automated and controls are simple.

To check the uniformity of a crystal specimen over the entire prepared surface thereof the specimen is preferably moved in a direction parallel to that surface such that the incident beam traces a spiral path over the surface.

The invention and preferred embodiment thereof will now be described by way of example with reference to the accompanying drawings in which.

Figure 1:
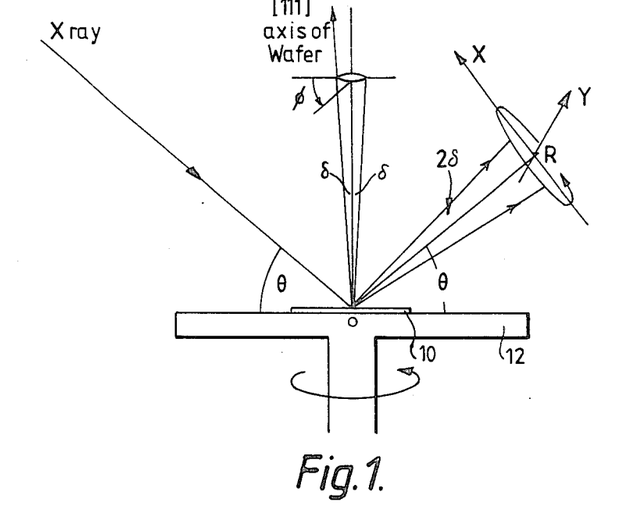
FIGS. 1 and 2 illustrate schematically the principles of the invention.
Figure 3:
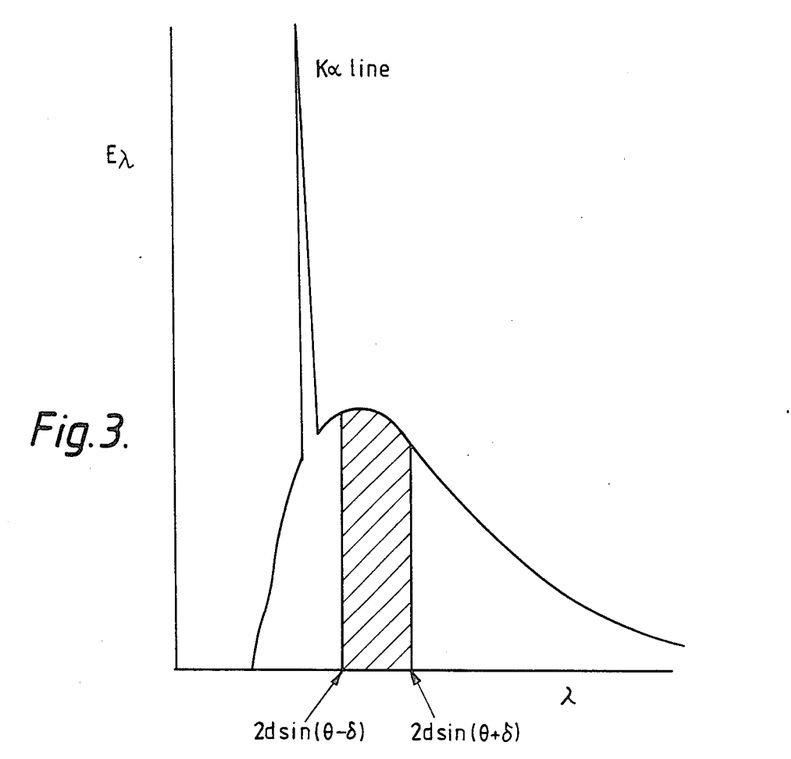
FIG. 3 is a typical X-ray spectrum showing the presence of a characteristic line and white radiation.

With reference now to FIGS. 1 and 3, the wafer 10 is placed on a horizontal turntable 12 which rotates the wafer in its own plane at between 100 and 400 rpm: the value is not critical. An X-ray diffraction tube and tubular collimator project a narrow pencil of unfiltered X-radiation (i.e. which may have a peak of characteristic K radiation) onto the wafer at O, and a flat-plate detector (e.g. a film, an image intensifier or position sensitive detector) is set at a symmetrical inclination to receive the reflected ray, OR. The scientific principles underlying this invention are summarised below:

(1) the geometrical laws of reflexion applied to a mirror whose normal precesses around a fixed axis; and (2) Bragg's Law which shows that X-ray diffraction fulfils the geometry of diffraction but occurs only for a specific wavelength from the X-ray spectrum.

The only complication lies in the peculiarly shaped trace of the reflected ray of the detector plane. For $\theta$, $\delta$, $\phi$, X, Y and D defined as in FIG. 1 we have:

$$X = D\left[\frac{\cos\phi \sin 2\delta - \sin 2\theta \sin^2\phi \sin^2\delta}{1 - 2\sin^2\delta (\sin^2\theta + \cos^2\theta \cos^2\phi)}\right]$$

$$Y = D\left[\frac{2\sin\phi \sin\delta (\sin\theta \cos\delta + \cos\theta \cos\phi \sin\delta)}{1 - 2\sin^2\delta (\sin^2\theta + \cos^2\theta \cos^2\phi)}\right]$$

In addition, if $\theta$ has been adjusted to reflect the K-alpha line from a perfectly cut wafer, the intense K-alpha spots for a miscut wafer occur when $$\cos\phi + \tan\theta.\tan(\delta/2)$$

$\delta$ is readily evaluated from the length 2X, of the major axis of the loop, $$\delta = 0.5[\arctan (X/D)]$$

But, because of the nonlinear nature of these equations, the evaluation of $\delta$ from the separation (2Y) between the K-alpha spots is strictly speaking an iterative process. In practice, however, the following approximation is sufficiently accurate when $\theta$ approximates to 45 deg. as recommended for other reasons in the specification.

$$\delta = \arctan (Y/D\sqrt{2})$$

e.g. for 2Y=27.2 mm, D=200 mm, $\theta$=45 deg. this equation gives =2.7529 deg., whereas a more refined calculation gives 2.7536 deg. These are indistinguishable in view of the limited precision of the data supplied.

The majority of industrially interesting materials to which this invention is applicable are cubic for which the desired axis is most often [111], occasionally also [100] or [110]. Other materials of industrial interest are trigonal or hexagonal, the commonest cutting planes being (0001), (10$\bar{1}$0), and (11$\bar{2}$0). It must be stressed here, however, that though for convenience reference is made hereinafter only to the (111) planes and [111] axes of a cubic material, the technique is in no way restricted; it applies to any reflexion and for any crystal symmetry. For many materials, however, best results are achieved if the surface film damaged by the cutting is polished or etched off first.

Figure 2:
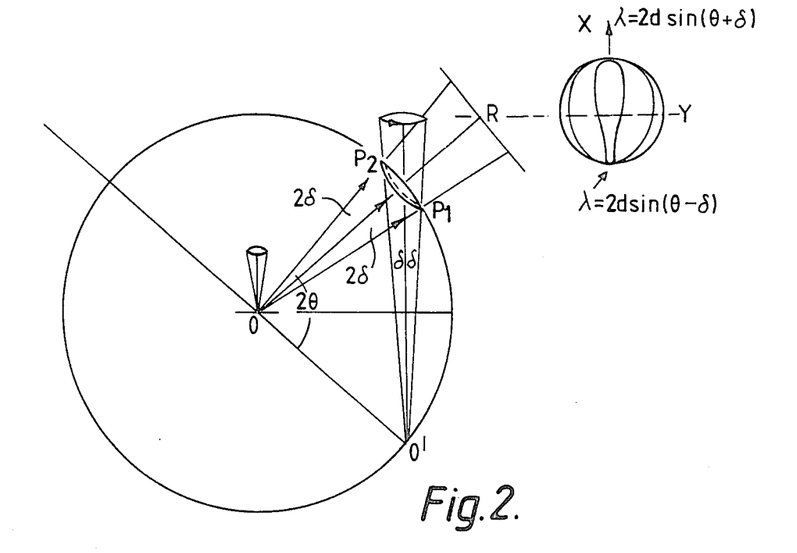

If there is no error between the rotation axis and the [111] axis, the latter rotates on itself and the reflexion geometry is maintained throughout the rotation. The detector, therefore, shows a single spot R. If, however, there is a cutting error, $\delta$, the [111] axis sweeps out a cone of semi-angle $\delta$ (see FIGS. 1 and 2) and the reflected ray sweeps out a "flattened cone" around OR whose semi-angle varies, being 2$\delta$ in the plane of incidence but decreasing off it—especially for low $\theta$. If the plane of the detector is set perpendicular to OR, then, as the table and wafer rotate, the spot on the detector traces out a loop, the right section of the "flattened cone". This is shown in FIG. 2, which is a central section through the reflection sphere and an illustration of the form of the loop for different values of $\theta$ and a common value of $\delta$. Examples of the loop are shown in FIG. 4 for $\theta$=45 deg. and errors, $\delta$, ranging from 1 to 10 degrees; and in FIG. 5 for an error of 10 deg. and 0 ranging from 10 to 80 degrees.

The loops are almost circular for $\theta$ above ca. 70 deg. then, as $\theta$ decreases, they become roughly elliptical and eventually very narrow and very asymmetrical across the y-axis. They are, however, always symmetrical across the x-axis, the major axis, and this axis extends Dtan (2$\delta$) on either side of the origin for all values of $\theta$, where D is the distance from the crystal to the detector. For reasons to be explained later it is preferable to work with values of $\theta$ in the vicinity of 45 deg., for which the loop is a perceptibly asymmetric oval (see FIG. 4).

Figure 6:
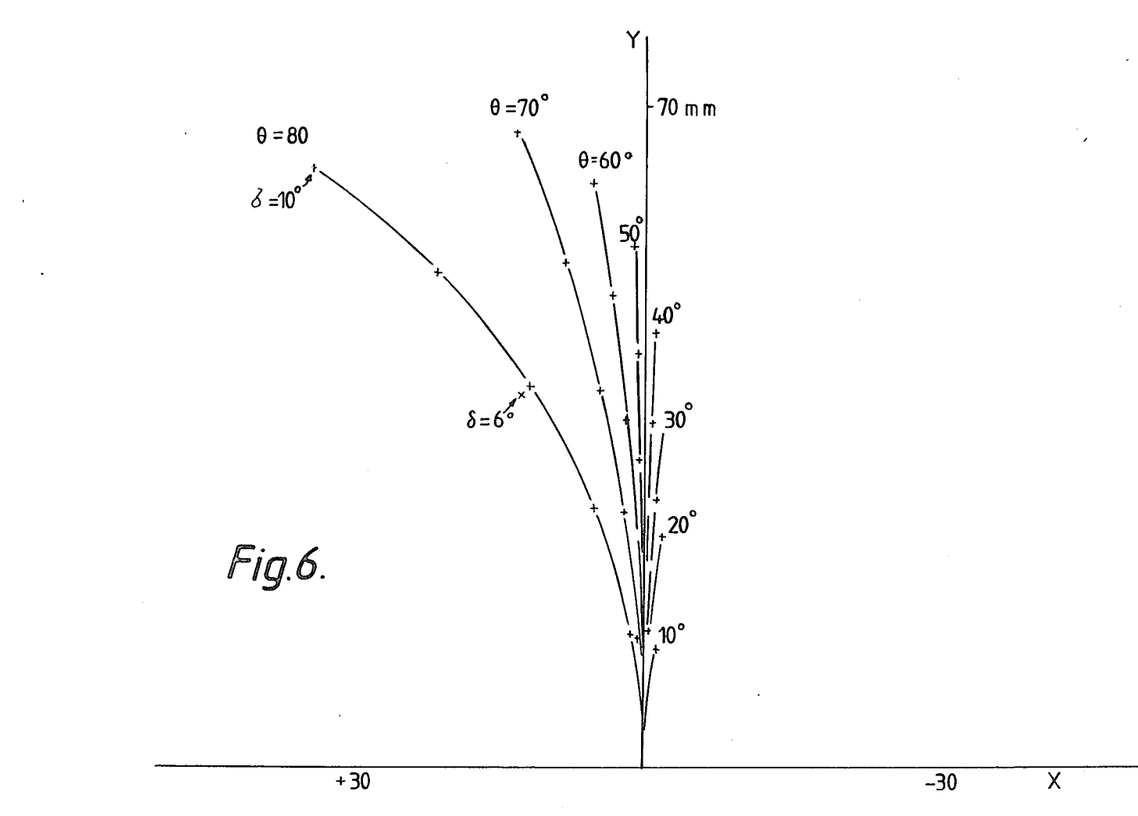
FIG. 6 shows the position of the K$\alpha$ spots for different combinations of $\theta$ and $\delta$.
Figure 7:
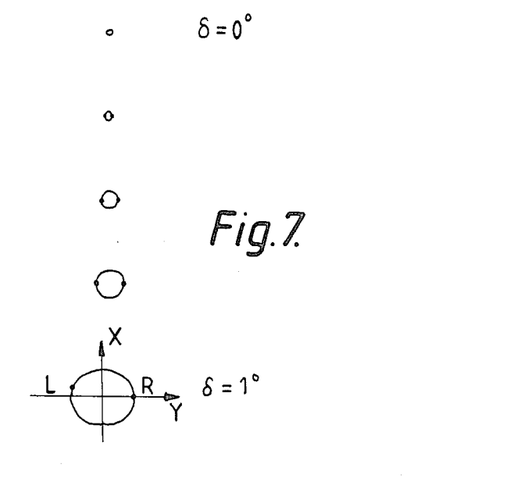
FIG. 7 illustrates how the oval or loop image expands with increasing cutting error.

In general the wavelength of the ray diffracted to any point on the oval comes from the continuous (white) part of the X-ray output and varies from 2dsin $(\theta-\delta)$, to 2dsin $(\theta+\delta)$ (see FIGS. 2 and 3). If this range includes a characteristic X-ray line as shown in FIG. 3, two symmetrically located bright spots flash out momentarily, at $(X, \pm Y)$ but at different times during the tracing of the oval. It is particularly convenient if the angles $\theta$ in FIG. 1 are preset for reflexion of the characteric component of the tube's output by, say, the (333) planes of the wafer material. For then, whereas the spot for a perfectly cut wafer is compact and uniformly intense throughout the rotation, any small cutting error expands the spot into a concentric oval whose perimeter is relatively faint (since it derives from the white component) except for the two intense spots that arise from the characteristic radiation: they occur at or near the opposite ends of the y-axis (see FIGS. 4 to 6). The break-up of the single steady bright spot and its conversion into a close pair which flash alternately is quite sensitive to cutting error. FIG. 7 shows how the image expands as the value of $\delta$ increases. The two bright spots, L, R, flash alternately as the wafer rotates. They usually lie close to the Y axis, but can deviate for large values of $\delta$ and $\theta$.

Figure 4:
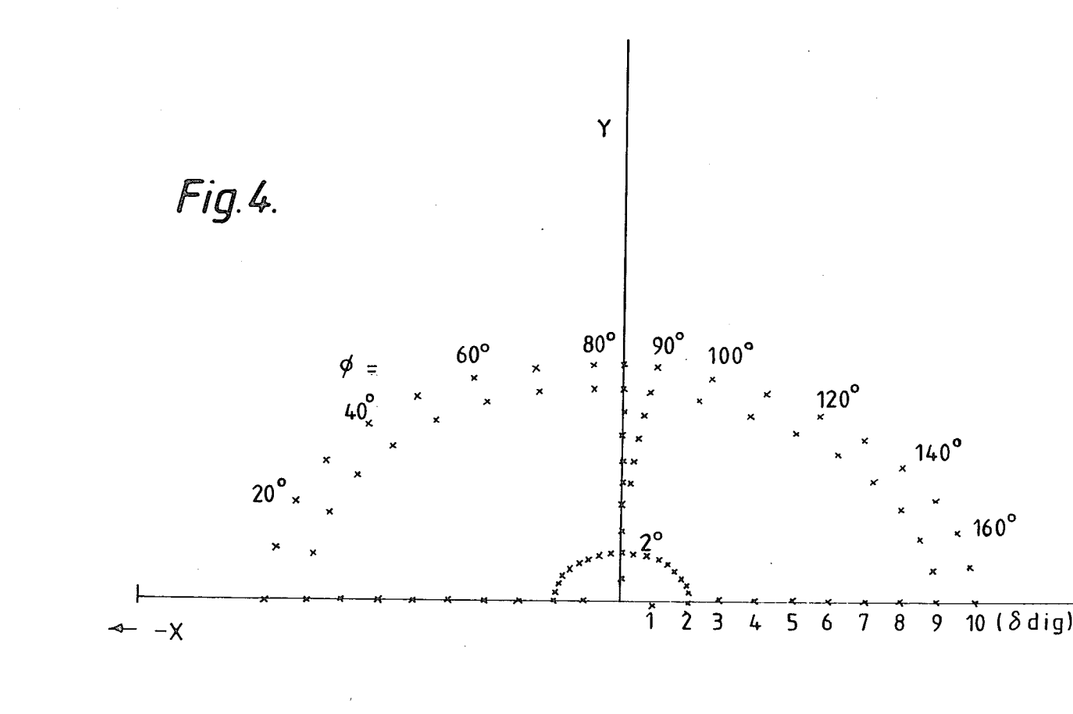
FIG. 4 illustrates the range of error ovals or loops traced on the detector for $\theta = 45°$ and $\delta$ ranging from 1° to 10°.
Figure 5:
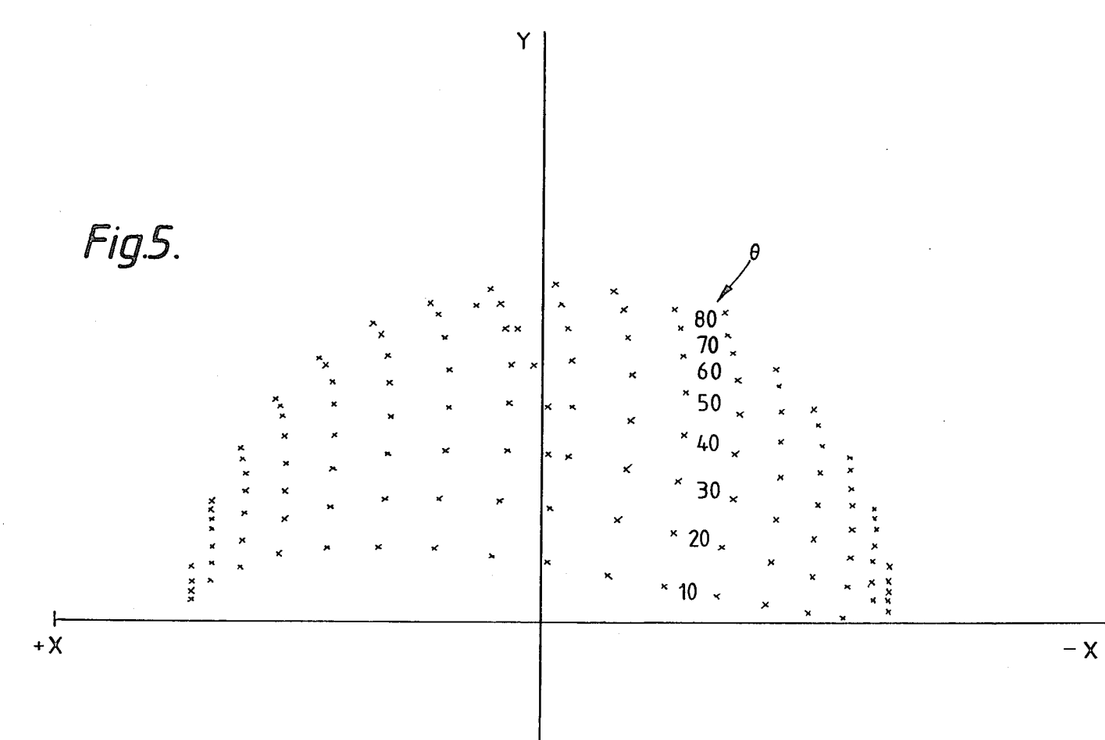
FIG. 5 illustrates the range of error ovals or loops for $\delta = 10°$ and $\theta$ ranging from 10° to 80°.

FIG. 4 shows for a number of possible error ovals the positions of the two "hotspots" on each: in this case ($\theta$=45 deg.) they all lie on the Y-axis. FIGS. 5 and 6 show how they diverge for other combinations of $\theta$ and $\delta$. The presence of two hotspots on an oval certifies that it is due to the (333) planes and is, therefore the oval we want. If the aperture of the detector is too large, or it is set too close to the wafer—or, if the cutting error is unusually large, one may observe additional concentric ovals due to reflexions from other adjacent sets of planes, but these are reflexions of much shorter wavelengths: the are faint and do not carry the tell-tale two strong spots—so no confusion should arise.

FIG. 1 was merely a schematic diagram for the purpose of explanation and a practical embodiment of the invention will now be described with reference to FIGS. 8, 9 and 10.

Figure 8:
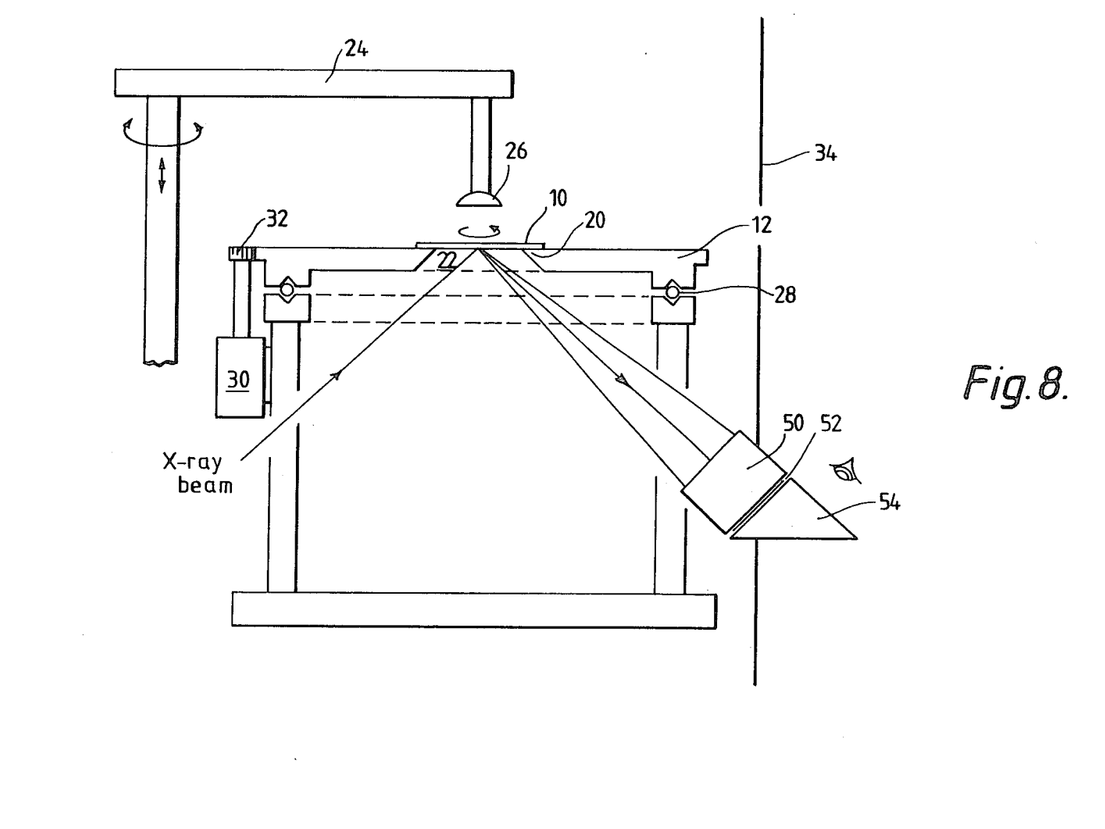
FIGS. 8 to 10 show schematically different parts of one embodiment of apparatus according to the invention.

Referring first to FIG. 8, the wafer 10 is supported on the bevelled lip 20 surrounding an aperture 22 in the turntable 12, with the face from which the reflexions are to occur facing downwards. This orientation avoids any angular error which could arise if the faces of the wafer were not accurately parallel. It also has the advantage of leaving the upper side of the turntable free so that a rotating arm 24 with a suction pad 26 may be provided to transfer wafers one at a time, from a stack to the turntable, and from the turntable to a sorting chute.

The turntable is supported on a ball race 28 and driven by an electric motor 30 provided with a gear 32 engaging a toothed ring on the outer edge of the turntable. Below the turntable the X-ray source and detector are disposed on a supporting mechanism and these components will be described below with reference to FIGS. 9 and 10. The whole apparatus is enclosed in a radiation screened enclosure, part of the shielding being indicated at 34.

Below the turntable is mounted a mechanism which is shown in more detail in FIGS. 9 and 10. It comprises a scissors jack having a pair of arms 40, 42 which can be raised or lowered symmetrically by means of a screw mechanism 44. The arm 40 carries an X-ray tube 46 and a collimator 48 and the arm 42 carries an image intensifier 50 provided with a graticule 52 and an inverting prism 54 which allows the image at the graticule to be viewed from a convenient angle through an opening in the radiation shield 34 (FIG. 8).

In one embodiment of the invention, the turntable and the supporting mechanism for the X-ray tube and detector are fixed in a rigid relation to each other so that the X-ray tube and collimator and the detector are always directed at a point on the crystal surface at the axis of rotation. In an alternative arrangement indicated in FIG. 9, one assembly, for example, the turntable, may be mounted on a trolley for limited motion so that the turntable may be moved in relation to the point of impingement of the X-ray beam causing the X-ray beam to trace out a spiral path on the surface of the wafer. This modification will be described in rather more detail below.

The setting up an operation of the apparatus will now be described.

The angles are first set to suit the wavelength and material by placing a perfectly cut standard wafer on the turntable and adjusting the scissors-jack device (FIG. 10) to pick up a sharp spot reflexion. This setting is only altered when it is necessary to work with wafers of a different material.

For visual grading, the image-intensifier viewing screen has attached to it a graticule marked with a line graduated in values of δ (cf. FIG. 4). The operator controls the destination of the wafer according to the observed length of the major-axis of the oval.

For automatic operation there are two alternative detectors.

Figure 11:
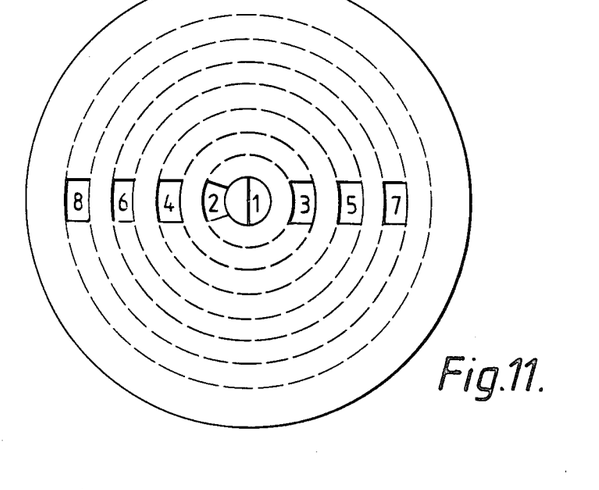
FIG. 11 shows a mask for use in quickly grading crystal specimens according to the length of the major axis of the error loop or oval.

(1) For grading, i.e. merely sorting the wafers into a series of ranges of δ, the viewing screen is covered by a mask that contains a number of slots (FIG. 11) spaced out along the major axis. Each slot passes light from a distinctive narrow range of possible ovals into a separate photo-detector. (The number, positions and widths of these slots is governed by the user's needs.) Usually only one photocell is activated at a time and controls the route taken by the wafer to the relevant collector. In the event of light entering two slots, the control is taken from the slot receiving the larger intensity. This device makes no use of characteristic radiation. It is relatively simple, inexpensive and easy to maintain, and it disposes of wafers at a brisk rate ca. 30/minute.

Figure 12:
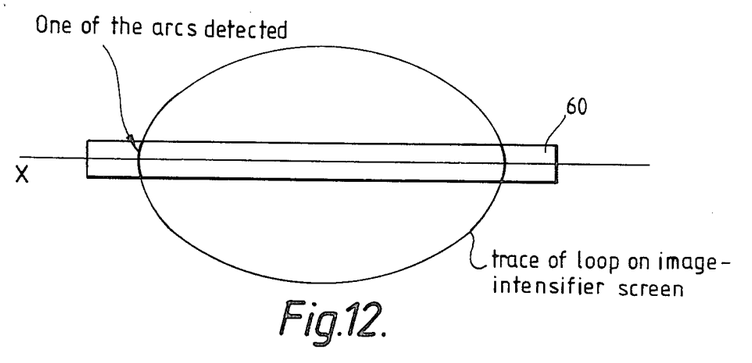
FIGS. 12 and 13 respectively illustrate alternative arrangements for a one-dimensional position sensitive detector for automatically measuring the dimensions of an error oval or loop.
Figure 13:
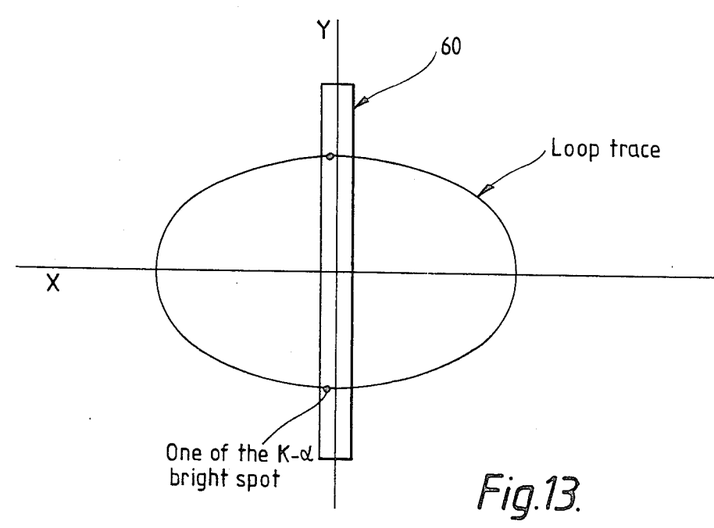

(2) On the other hand, if one needs to measure the dimensions of an oval automatically and to a precision higher than the above mask allows, a one-dimensional position-sensitive detector is used, arranged as in either FIGS. 12 or 13.

In the arrangement of FIG. 12, the aperture of the detector is indicated at 60. The detector measures the major axis and relies solely on white radiation. Its pulse-height analyser "window" must be wide enough to accept photons corresponding to the wavelength range, 2dsin $(\theta-\delta)$ to 2dsin $(\theta+\delta)$, for the maximum error likely to be encountered.

The alternative position (FIG. 13) is used for measuring the separation of the two bright spots on an oval. Their positions on typical ovals, shown in FIGS. 5 and 6, stray outside the aperture of the detector if the values of $\theta$ are well removed from 45 degrees and the errors are large. For $\delta \leq 5$ deg., the range of $\theta$ allowable for the typical aperture shown in FIG. 6 is ca. 45±20 deg; this offers ample scope for finding a suitable reflexion.

Thus, for silicon and germanium it is possible to take advantage of a convenient relation between their lattice parameters and the wavelength of Copper K-alpha radiation. The Bragg angles for the (333) reflexions are 45.077 deg. for germanium and 47.527 deg. for silicon, and, as shown in Table 1, the deviations of the two hotspots from the y-axis are insignificant in relation to the breadth of the hotspot, even for a cutting error of 5 degree.

TABLE 1

| Error (Deg.) | X (mm) | ± Y (mm) | Co-ordinates of a Kα spot |
|---|---|---|---|
| | Theta = 45.077° | | Germanium and CuKα radn. |
| 1 | .000 | 4.944 | |
| 2 | .000 | 9.894 | |
| 3 | .001 | 14.858 | |
| 4 | .002 | 19.841 | |
| 5 | .004 | 24.850 | |
| 6 | .005 | 29.892 | |
| 7 | .008 | 34.973 | |
| 8 | .010 | 40.102 | |
| 9 | .013 | 45.285 | |
| 10 | .016 | 50.530 | |
| | Theta = 47.527° | | Silicon and CuKα radn. |
| 1 | .005 | 5.150 | |
| 2 | .023 | 10.308 | |
| 3 | .052 | 15.480 | |
| 4 | .094 | 20.675 | |
| 5 | .147 | 25.899 | |
| 6 | .213 | 31.160 | |
| 7 | .291 | 36.467 | |
| 8 | .382 | 41.827 | |
| 9 | .486 | 47.249 | |
| 10 | .604 | 52.742 | |

In such cases, the hotspots remain within the aperture of the detector for the whole range of likely cutting errors. The pulse-height analyser window is, therefore, set to accept only the characteristic radiation with the result that the detector system observes only the two characteristic spots: it ignores the asymmetrical "white" parts of the same oval and also those parts of any other ovals that may enter the aperture. The linear separation of the two hotspots, which are of course recorded at different times, can be converted by the detector systems's own microcomputer into the desired measure of error and used if necessary for control purposes.

Both automatic devices deal with wafers at similar rates. But, though the linear position-sensitive detector is more expensive than that used in the first (masked) automatic version, it offers a much higher degree of angular resolution.

The devices described above measure the cutting error at one point on the wafer, namely the point on the rotation axis of the table. The principle can be applied to scanning the entire area of a wafer as shown in FIG. 9.

Figure 9:
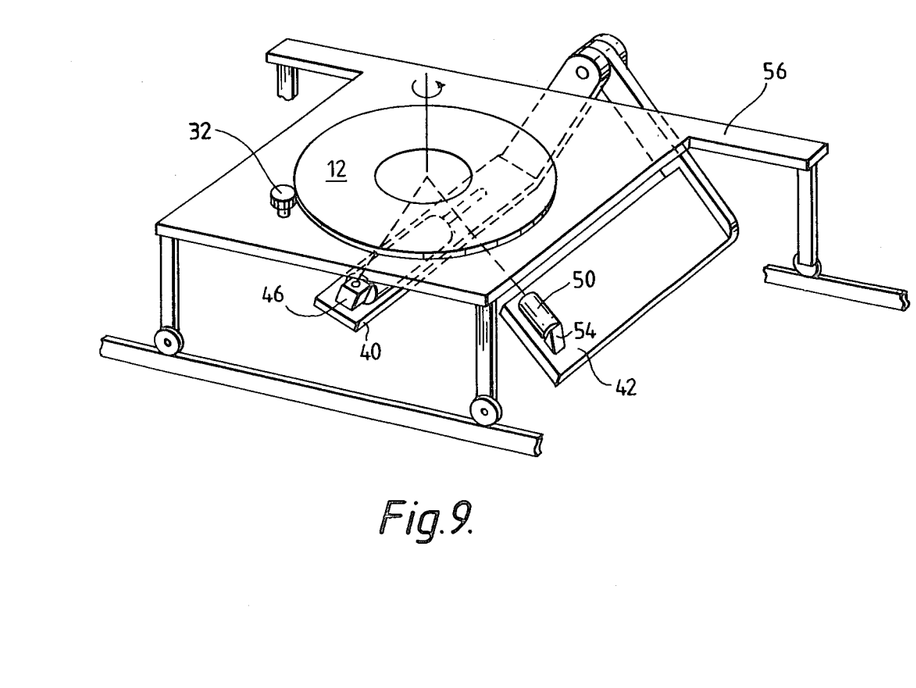
Figure 10:
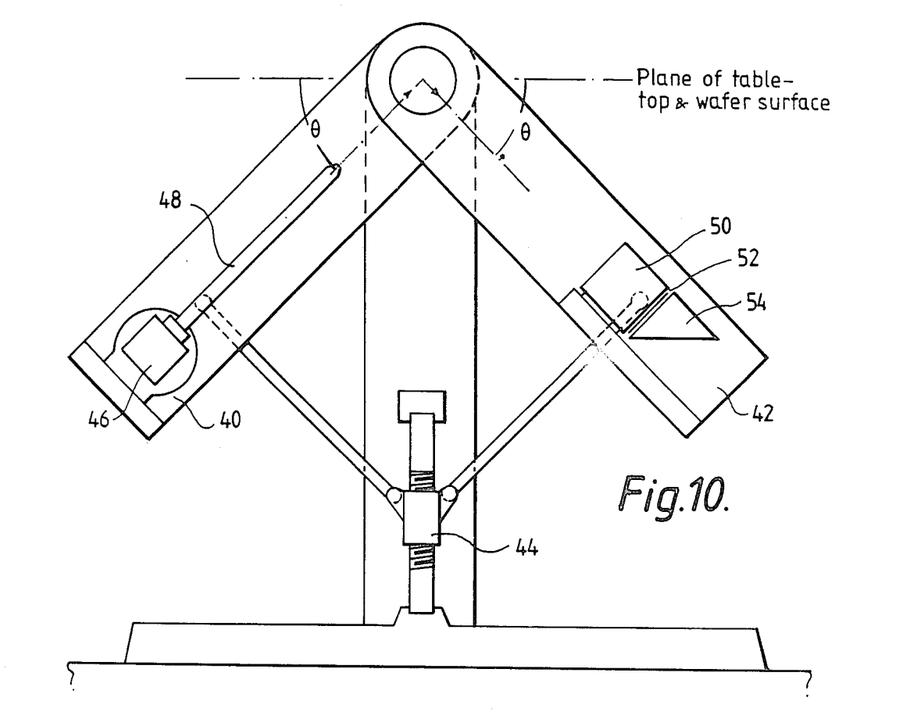

The only modification needed in FIG. 9 is to fit wheels to the trolley 56 that carries the rotating table so that it can be moved on rails parallel to the plane of incidence. The point of impact of the beam is thus moved outward from the rotation axis along a radius, and, since the table is simultaneously rotating, the point of impact traces out a spiral locus on the surface of the wafer. As the wafer makes one rotation the reflected ray traces an oval, but this time each point on the oval corresponds to a distinct point on one turn of the spiral. First, a reference oval is obtained for one revolution with the point of impact on the axis of rotation. Then the motion along the rails begins and, if the cutting error is uniform throughout the wafer, the ovals from all subsequent turns of the spiral overlie the reference oval. However, if there are discontinuities in the orientation they will reveal themselves by wanderings of the reflection from the reference oval, and possibly also by movements of the two bright spots—if they occur. A Polaroid camera is a convenient detector in this context as it integrates all these traces and produces a record quickly and relatively cheaply. An alternative is either a vidicon reading a fluorescent screen or an image—intensifier feeding a storage tube which accumulates the traces from the whole spiral. This is more expensive to install but can be made completely automatic, whereas a Polaroid camera requires a human operator, is less sensitive and therefore requires longer exposures, and involves the running costs of film.

For a trolley advancing at 4 mm/sec. it takes 12.5 sec to complete a spiral to a radius of 50 mm. So allowing for the time taken to record the reference circle and to reposition the table to allow the wafer to be changed, each wafer takes about 20–30 seconds.

All these detectors have, however, one limitation, namely that, though they can indicate whether the orientation is uniform or not—and usually that is all one needs to know—they do not map the discontinuities.

If mapping is needed, the spiral scanner of FIG. 9 can be used, but one must use a two-dimensional position-sensitive detector, (the linear position-sensitive detector described above is useless in this context). Again, a reference oval is recorded when the point of impact is on the rotation axis, and this oval is held in the memory of the detector's computer. Then, during the spiral scan, any significant departure from the reference oval will be noted and the computer can correlate it with the position on the spiral of the point of impact of the X-ray beam at that instant.

Figure 14:
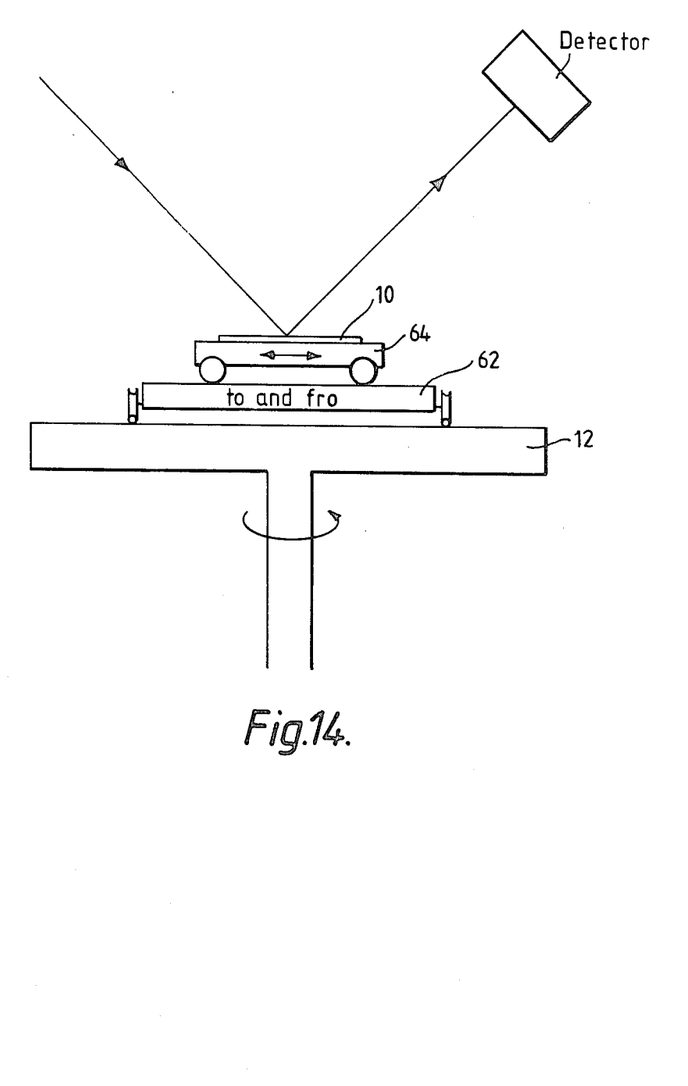
FIG. 14 shows schematically a modified embodiment of apparatus according to the present invention.

An alternative arrangement is depicted in FIG. 14, in which the point of impact of the X-ray beam is always on the axis of rotation and the wafer 10 rest on two trolleys 62,64 that translate it into two mutually perpendicular directions relative to the rotation of the turntable 12.

In this case, it does not matter if the prepared face is not perpendicular to the axis of rotation for we are not now interested in the accuracy of the estimate of $\delta$, only to check the constancy of the loop for all points on the wafer. It is therefore possible to take reflexions off the top face of the wafer.

The wafer is stepped laterally after every two or three revolutions.

An X, Y scan such as this is, therefore, slower than a spiral scan, but is more informative. Thus, each loop is a true record of the state of affairs at a single point of impact, the whole loop changes—not just a part of it as happens for the spiral scan—, if the magnitude of $\delta$ changes. In addition a change in the relationship of the major axis and the position of the bright spots to the $\phi$ values betrays a rotation of the crystallographic axis relative to the wafer. Monitoring is particularly conveniently done by following both the separation of the K-alpha spots and the $\phi$ values at which they occur.

With the table carrying a burden whose centre of gravity is constantly shifting it is necessary to slow the rotation rate of the table. If the steps are 4 mm in both directions and 2 revolutions are used for each point scanned, an area of 10 cm × 10 cm takes ca. 30 minutes.

The arrangement of FIG. 14 is more complicated and expensive to construct, but may be needed in certain investigations.

We claim:

1. A method of measuring the deviation between the normal to a surface of a crystal and a crystallographic axis of the crystal, the method comprising the steps of:
   (a) rotating continuously the crystal about said normal;
   (b) directing an X-ray beam at said surface at an axis of rotation of the crystal thereby creating a reflected beam and defining a plane of incidence;
   (c) detecting the reflected X-ray beam at said surface by means of a position sensitive detector perpendicular to the reflected beam and positioned in the plane of incidence;
   (d) determining a dimension of a characteristic figure traced by the reflected beam at the detector as the crystal is rotated;
   (e) determining from said traced characteristic figure the deviation between the axis of rotation of the crystal and the crystallographic axis.

2. Method according to claim 1 in which angles of incidence and reflection of said X-ray beam upon the crystal are substantially 45°.

3. Method according to claim 1 in which the major axis of the traced characteristic figure is measured and the deviation is computed therefrom.

4. Method according to claim 1 in which the spectrum of the X-ray beam contains a characteristic line, the traced characteristic figure contains a pair of bright spots, and the separation of the bright spots is measured and the deviation is computed therefrom.

5. Method according to claim 1 in which the crystal is translated in its own plane between rotations so as to compare deviations at different points of the surface.

6. Method according to any preceding claim in which the crystal is a slice cut from a single crystal and the cut surface is etched or polished to remove the damaged surface film before measurement.

7. The method of claim 1 further including the step of loading and unloading the crystal by the use of a rotating arm with a suction means adapted to engage the crystal.

8. The method of claim 4 in which angles of incidence and reflection for said X-ray beam containing a characteristic line are determined by Bragg's law.

9. Method of measuring the deviation between a normal to a surface of a crystal and a crystallographic axis of the crystal, the method comprising the steps of:
   (a) rotating continuously the crystal about the normal;
   (b) directing an X-ray beam at a point of impact on the surface thereby creating a reflected beam and defining a plane of incidence;
   (c) detecting the reflected X-ray beam at the surface by means of a position-sensitive detector perpendicular to the reflected beam and positioned in the plane of incidence;
   (d) determining a dimension of a characteristic figure traced by the reflected beam at the detector as the crystal is rotated;
   (e) determining from said traced characteristic figure the deviation between the axis of rotation of the crystal and the crystallographic axis;
   (f) changing the distance between the point of impact and the axis of rotation as the crystal rotates so that the point of impact traces a spiral path in the crystal surface;
   (g) determining from said spiral path the deviation at different points of the surface.

10. Apparatus for measuring the deviation between a normal to a surface of a crystal and a crystallographic axis of the crystal, comprising a turntable rotatable about an axis, means for supporting the crystal at the axis of rotation of the turntable, an X-ray source directed at the surface of the crystal at the axis of rotation of the turntable, an X-ray detector for detecting the X-rays from the source after reflection by the crystal, and means for determining the path traced by the reflected X-rays during rotation of the crystal by said turntable.

11. Apparatus according to claim 10 further including an adjustable support for the X-ray source, an adjustable support for the X-ray detector, coupling means coupling the X-ray source support and the X-ray detector support for movement symmetrical with respect to the crystal supporting means, and actuating means for simultaneously moving the X-ray source and X-ray detector.

12. The apparatus of claim 10 further including a rotating arm for loading and unloading the crystal to and from said supporting means, said rotating arm including a suction means adapted to engage the crystal.

13. Apparatus according to claim 10 further including means for translating the crystal during rotation in a direction transverse to the axis of rotation of the turntable.

* * * * *